(12) United States Patent
Wiemann

(10) Patent No.: US 10,179,061 B2
(45) Date of Patent: Jan. 15, 2019

(54) FOOT PIVOTING DEVICE

(71) Applicant: Donald Wiemann, Green Valley, AZ (US)

(72) Inventor: Donald Wiemann, Green Valley, AZ (US)

(*) Notice: Subject to any disclaimer, the term of this patent is extended or adjusted under 35 U.S.C. 154(b) by 359 days.

(21) Appl. No.: 15/052,838

(22) Filed: Feb. 24, 2016

(65) Prior Publication Data
US 2017/0239073 A1 Aug. 24, 2017

(51) Int. Cl.
*A61F 5/01* (2006.01)

(52) U.S. Cl.
CPC .................................. *A61F 5/0113* (2013.01)

(58) Field of Classification Search
CPC .... A61F 5/0113; A61F 5/0102; A61F 5/0585; A61F 5/0127
See application file for complete search history.

(56) References Cited

U.S. PATENT DOCUMENTS

| | | | |
|---|---|---|---|
| 2,871,852 A | 2/1959 | Miller | |
| 4,252,112 A | 2/1981 | Joyce | |
| 5,382,224 A * | 1/1995 | Spangler | A61F 5/0113 602/23 |
| 5,647,827 A * | 7/1997 | Gutkowski | A63B 21/0004 482/122 |
| 6,361,517 B1 * | 3/2002 | Slinger | A61F 5/0113 36/140 |
| 6,428,495 B1 | 8/2002 | Lynott | |
| 6,551,221 B1 * | 4/2003 | Marco | A63B 21/0004 280/600 |
| D514,225 S | 1/2006 | Sassi | |
| 8,353,807 B2 | 1/2013 | Kruijsen et al. | |
| 8,382,694 B2 | 2/2013 | Wenger | |

FOREIGN PATENT DOCUMENTS

EP          1231873        11/2000

* cited by examiner

*Primary Examiner* — Ophelia A Hawthorne

(57) ABSTRACT

A foot pivoting device for correcting drop foot includes a belt that is configured to extend around a waist of a person, such that the belt is supported on the waist of the person. The device also comprises a strap that has a first end and a second end. The first end is couplable to the belt such that the strap is configured to extend along a front side of a leg of the person. A fastener is coupled to the second end of the strap. The fastener is configured to couple the second end of the strap to a shoe worn by the person proximate to a front end of the shoe. The front end of the shoe is pivoted upwardly when the leg of the person is pivoted forwardly at the hip.

9 Claims, 5 Drawing Sheets

FOOT PIVOTING DEVICE

BACKGROUND OF THE DISCLOSURE

Field of the Disclosure

The disclosure relates to foot pivoting devices and more particularly pertains to a new foot pivoting device for correcting drop foot.

SUMMARY OF THE DISCLOSURE

An embodiment of the disclosure meets the needs presented above by generally comprising a belt that is configured to extend around a waist of a person, such that the belt is supported on the waist of the person. The device also comprises a strap that has a first end and a second end. The first end is couplable to the belt such that the strap is configured to extend along a front side of a leg of the person. A fastener is coupled to the second end of the strap. The fastener is configured to couple the second end of the strap to a shoe worn by the person proximate to a front end of the shoe. The front end of the shoe is pivoted upwardly when the leg of the person is pivoted forwardly at the hip.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
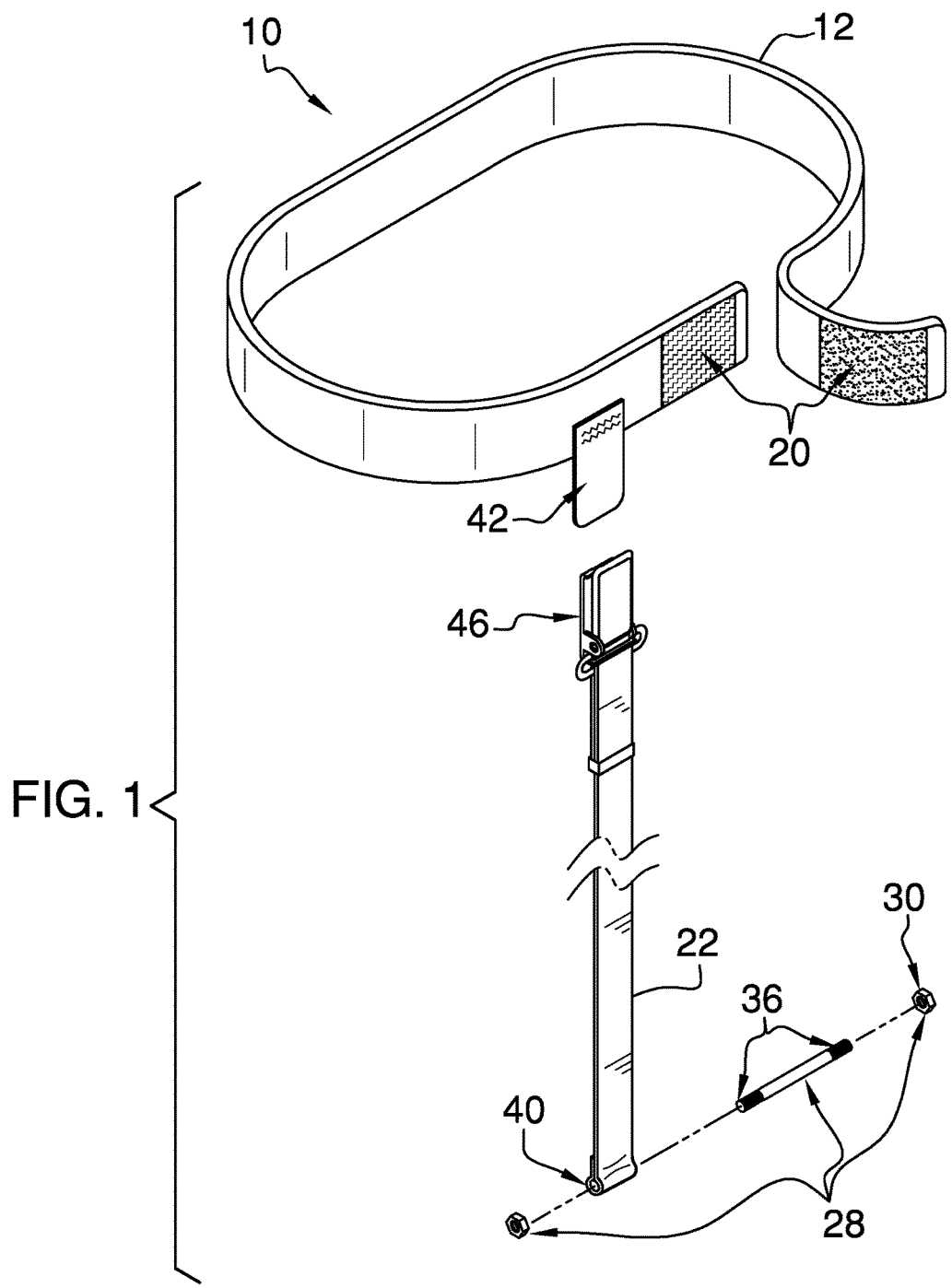
FIG. 1 is an isometric perspective view of a foot pivoting device according to an embodiment of the disclosure.
Figure 2:
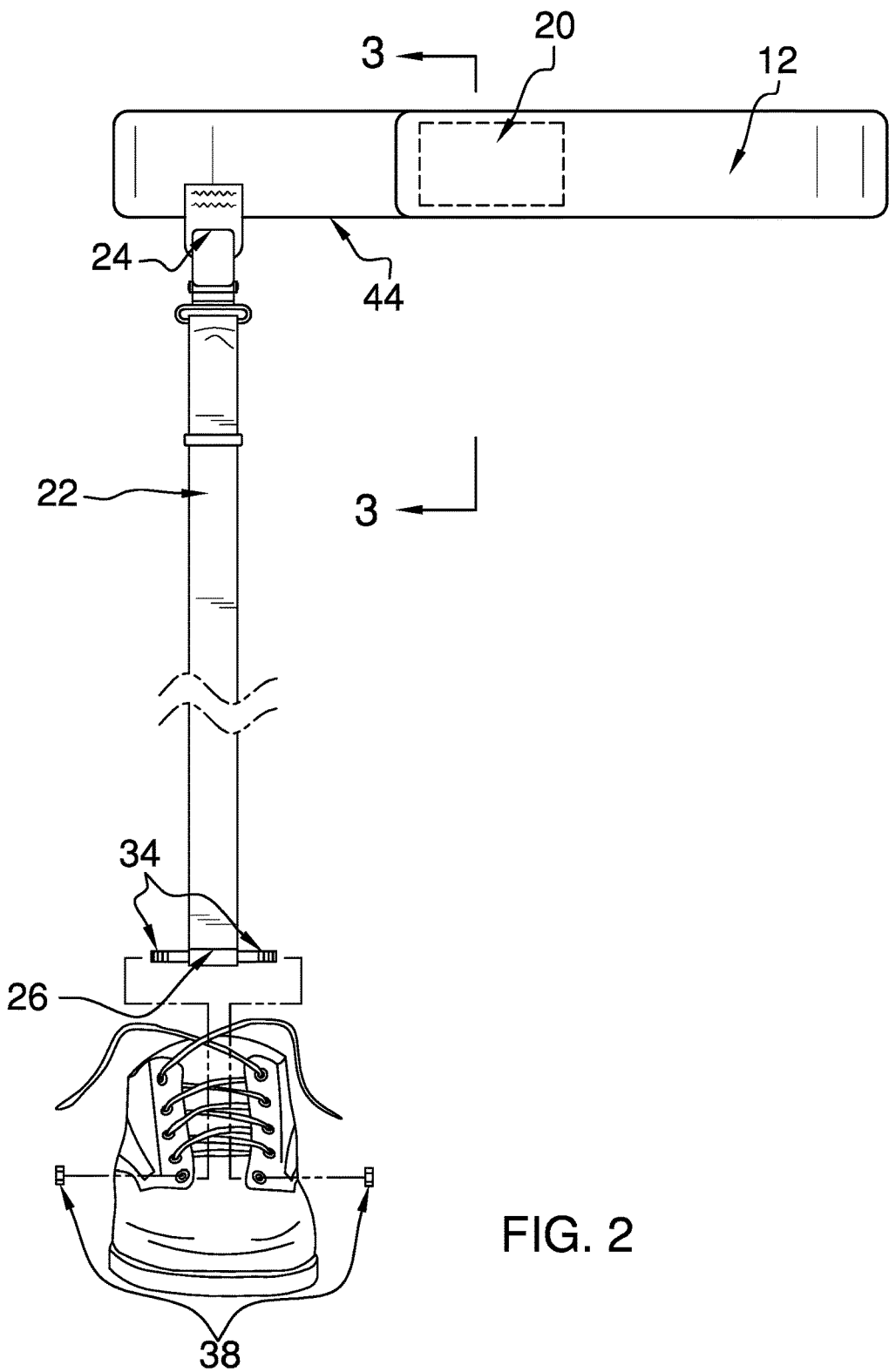
FIG. 2 is a front view of an embodiment of the disclosure.
Figure 3:
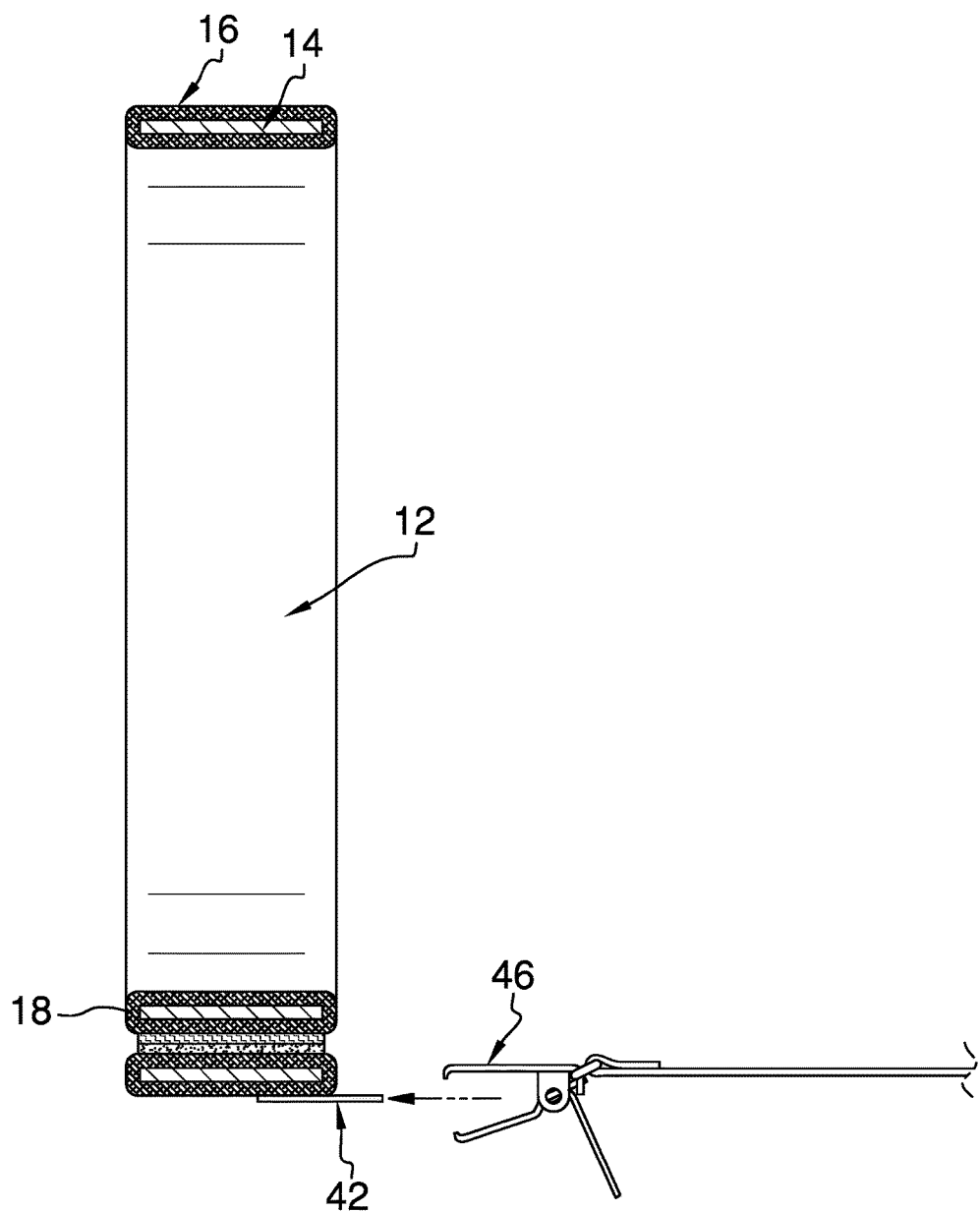
FIG. 3 is a cross-sectional view of an embodiment of the disclosure.
Figure 4:
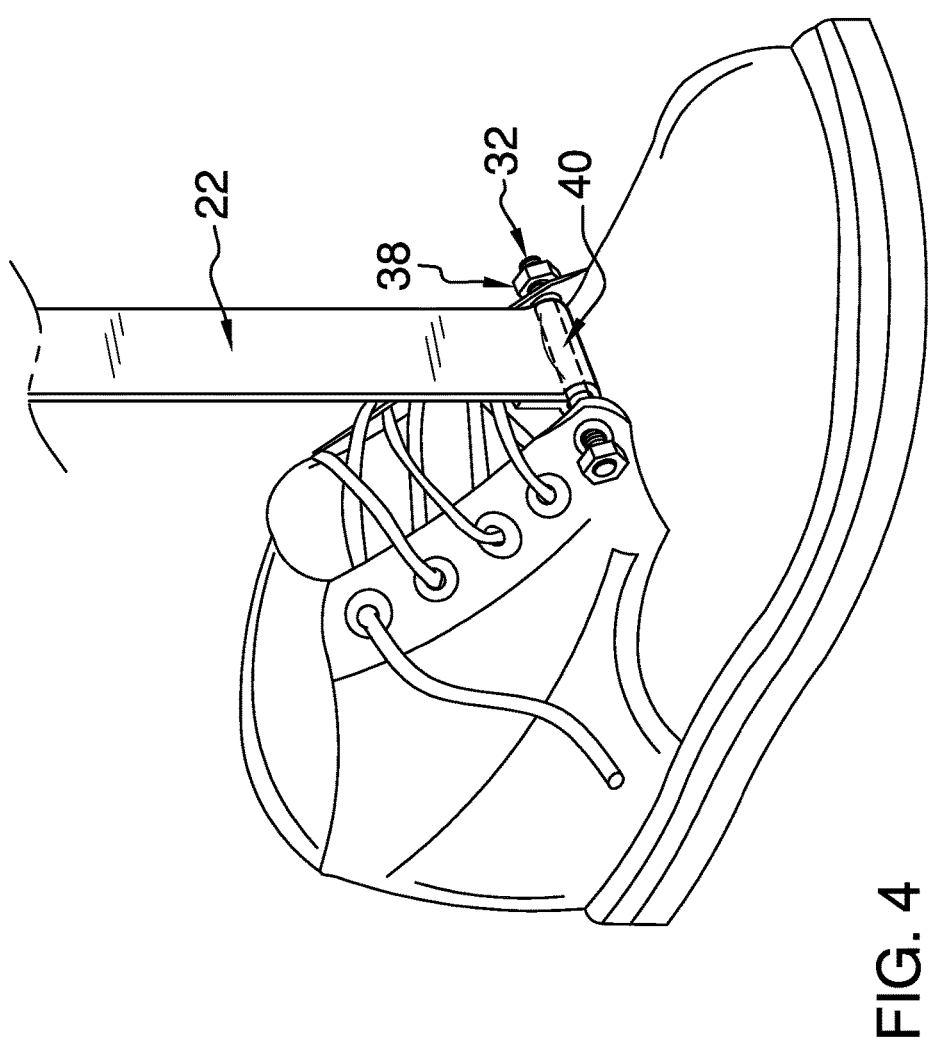
FIG. 4 is a detail view of an embodiment of the disclosure.
Figure 5:
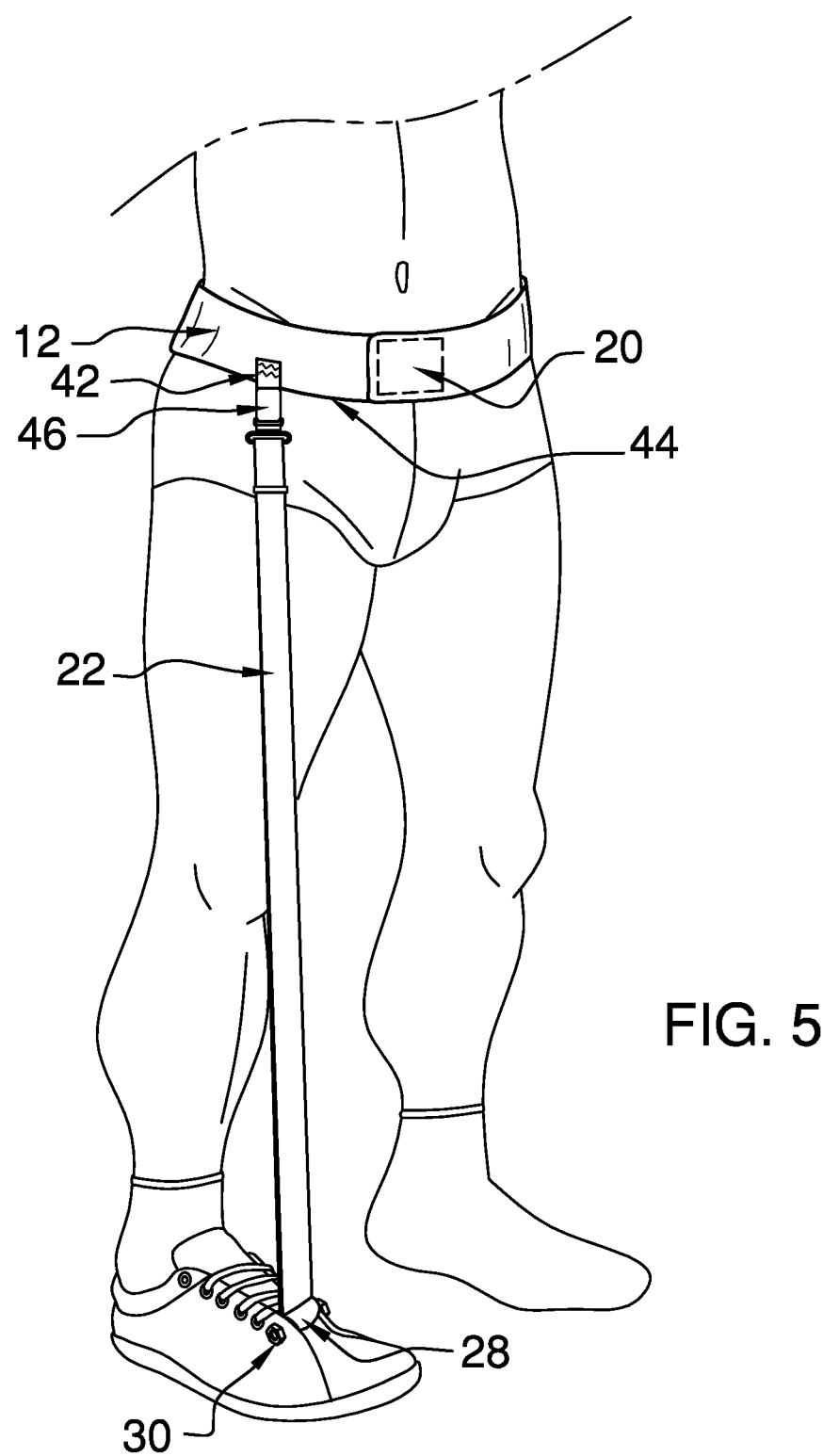
FIG. 5 is an in-use view of an embodiment of the disclosure.

With reference now to the drawings, and in particular to FIGS. 1 through 5 thereof, a new foot pivoting device embodying the principles and concepts of an embodiment of the disclosure and generally designated by the reference numeral 10 will be described.

As best illustrated in FIGS. 1 through 5, the foot pivoting device 10 generally comprises a belt 12 that is configured to extend around a waist of a person such that the belt 12 is supported on the waist of the person. The belt 12 has a core 14 and a covering 16 that extends over the core 14. Preferably, the covering 16 comprises a soft material 18. Also preferably, complementary portions of hook and loop fastener 20 are positioned on the belt 12 such that the belt 12 is configured to couple to the person around the waist of the person.

The device 10 also comprises a strap 22 that has a first end 24 and a second end 26. The first end 24 is couplable to the belt 12 such that the strap 22 is configured to extend along a front side of a leg of the person. The strap 22 has an adjustable length and is resilient. Preferably, the strap 22 comprises elastic. A fastener 28 is coupled to the second end 26 of the strap 22. Preferably, the fastener 28 comprises a connector 30 and a pin 32 that has opposite ends 34. The pin 32 is elongated such that the pin 32 is configured to be positioned to extend through aligned eyelets of the shoe. Opposite end sections 36 of the pin 32 are threaded. The connector 30 is couplable to the pin 32 such that the connector 30 is configured to secure the pin 32 to the shoe. The connector 30 comprises a pair of nuts 38. Each nut 38 is threadedly engagable to an associated one of the opposite end sections 36 of the pin 32.

A channel 40 extends through the second end 26 of the strap 22. The pin 32 extends through the channel 40. A tab 42 is coupled to and extends laterally outward from a longitudinal edge 44 of the belt 12. The first end 24 of the strap 22 is couplable to the tab 42. A clip 46 is mounted to the first end 24 of the strap 22. The clip 46 is engagable to the tab 42 such that the first end 24 of the strap 22 is coupled to the tab 42.

In use, the belt 12 is configured to be positioned around the waist of the user and secured to the user with the complementary portions of hook and loop fastener 20. The fastener 28 coupled to the second end 26 of the strap 22 is configured to be coupled to a shoe worn by the person proximate a front end of the shoe. The clip 46 is positioned to couple to the tab 42, such that the user's shoe is elastically coupled at the front end to the belt 12. The front end of the shoe is pivoted upwardly when the leg of the person is pivoted forwardly at the hip.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A foot pivoting device comprising:
    a belt configured for extending around a waist of a person such that said belt is supported on the waist of the person, said belt having a core and a covering extending over said core, said covering comprising a soft material;

a strap having a first end and a second end, said first end being couplable to said belt such that said strap is configured for being positioned to extend along a front side of a leg of the person;

a fastener coupled to said second end of said strap wherein said second end of said strap is configured for being coupled to a shoe worn by the person proximate a front end of the shoe such that said front end of said shoe is pivoted upwardly when the leg of the person is pivoted forwardly at a hip of the person, said fastener comprising
- a pin having opposite ends, said pin being elongated such that said pin is configured for being positioned to extend through aligned eyelets of the shoe, and
- a connector couplable to said pin wherein said connector is configured for securing said pin to the shoe; and a tab coupled to and extending laterally outward from a longitudinal edge of said belt, said first end of said strap being couplable to said tab.

2. The device of claim 1, further comprising a channel extending through said second end of said strap, said pin extending through said channel.

3. The device of claim 1, further comprising:
opposite end sections of said pin being threaded; and
said connector comprising a pair of nuts, each said nut being threadedly engagable to an associated one of said opposite end sections of said pin.

4. The device of claim 1, further comprising a clip mounted to said first end of said strap, said clip being engagable to said tab such that said first end of said strap is coupled to said tab.

5. The device of claim 1, further comprising complementary portions of hook and loop fastener positioned on said belt wherein said belt is configured for coupling to the person around the waist of the person.

6. The device of claim 1, further comprising said strap having an adjustable length.

7. The device of claim 1, further including said strap being resilient.

8. The device of claim 1, further including said strap comprising elastic.

9. A foot pivoting device comprising:

a belt configured for extending around a waist of a person such that said belt is supported on the waist of the person, said belt having a core and a covering extending over said core, said covering comprising a soft material;

a strap having a first end and a second end, said first end being couplable to said belt such that said strap is configured for being positioned to extend along a front side of a leg of the person, said strap having an adjustable length, said strap being resilient, said strap comprising elastic; and a fastener coupled to said second end of said strap wherein said second end of said strap is configured for being coupled to a shoe worn by the person proximate a front end of the shoe such that said front end of said shoe is pivoted upwardly when the leg of the person is pivoted forwardly at a hip of the person, said fastener comprising:
- a pin having opposite ends, said pin being elongated such that said pin is configured for being positioned to extend through aligned eyelets of the shoe, opposite end sections of said pin being threaded, and
- a connector couplable to said pin wherein said connector is configured for securing said pin to the shoe, said connector comprising a pair of nuts, each said nut being threadedly engagable to an associated one of said opposite end sections of said pin;

a channel extending through said second end of said strap, said pin extending through said channel;

a tab coupled to and extending laterally outward from a longitudinal edge of said belt, said first end of said strap being couplable to said tab;

a clip mounted to said first end of said strap, said clip being engagable to said tab such that said first end of said strap is coupled to said tab;

complementary portions of hook and loop fastener positioned on said belt wherein said belt is configured for coupling to the person around the waist of the person.

* * * * *